United States Patent [19]

Eidenschink et al.

[11] 4,302,352
[45] Nov. 24, 1981

[54] FLUOROPHENYLCYCLOHEXANES, THE PREPARATION THEREOF AND THEIR USE AS COMPONENTS OF LIQUID CRYSTAL DIELECTRICS

[75] Inventors: Rudolf Eidenschink, Dieburg; Ludwig Pohl, Darmstadt, both of Fed. Rep. of Germany

[73] Assignee: Merck Patent Gesellschaft mit Beschränkter Haftung, Darmstadt, Fed. Rep. of Germany

[21] Appl. No.: 123,628

[22] Filed: Feb. 22, 1980

[30] Foreign Application Priority Data

Feb. 24, 1979 [DE] Fed. Rep. of Germany ....... 2907332

[51] Int. Cl.³ .......................... C09K 3/34; G02F 1/13; C07C 49/43; C07C 49/80; C07C 23/18
[52] U.S. Cl. .............................. 252/299.63; 252/299.5; 568/329; 570/129; 350/350 R
[58] Field of Search ................. 570/129; 568/329; 252/299.63, 299.5; 350/350 R

[56] References Cited

U.S. PATENT DOCUMENTS

| | | | |
|---|---|---|---|
| 3,979,321 | 9/1976 | Couttet et al. | 252/299.5 |
| 3,983,049 | 9/1976 | Aftergut et al. | 252/299.5 |
| 4,011,173 | 3/1977 | Steinstrasser | 252/299.5 |
| 4,018,507 | 4/1977 | Raghavam | 252/299.5 |
| 4,047,803 | 9/1977 | Yaguchi et al | 252/299.5 |
| 4,048,088 | 9/1977 | Yaguchi et al. | 252/299.5 |
| 4,118,335 | 10/1978 | Krause et al. | 252/299.5 |
| 4,130,502 | 12/1978 | Eidenschink et al. | 252/299.63 |
| 4,198,130 | 4/1980 | Boller et al. | 252/299.5 |
| 4,228,029 | 10/1980 | Osman | 252/299.5 |
| 4,229,315 | 10/1980 | Krause et al. | 252/299.63 |

FOREIGN PATENT DOCUMENTS

51-33785 3/1976 Japan ................ 252/299.5

*Primary Examiner*—Teddy S. Gron
*Attorney, Agent, or Firm*—Millen & White

[57] ABSTRACT

Fluorophenylcyclohexanes of the formula

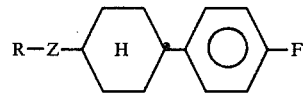

wherein R is alkyl of 1 to 17 carbon atoms and Z is carbonyl or methylene, are valuable components for use in liquid crystal dielectrics.

9 Claims, No Drawings

FLUOROPHENYLCYCLOHEXANES, THE PREPARATION THEREOF AND THEIR USE AS COMPONENTS OF LIQUID CRYSTAL DIELECTRICS

BACKGROUND OF THE INVENTION

For liquid crystal display elements, the properties of nematic or nematic-cholesteric liquid crystal materials are utilized to effect a significant change in their optical properties, such as light transmission, light scattering, double refraction, reflectance or color, under the influence of electrical fields. The function of such display elements is based, for example, on the phenomenon of dynamic scattering, the deformation of oriented phases, the Schadt-Helfrich effect in the twisted cell or the nematic-cholesteric phase transition.

For industrial application of these effects in liquid crystal display elements, liquid crystal materials which must meet a large number of requirements are needed. Particularly important requirements are chemical stability towards moisture, air and physical influences, such as heat, radiation in the infrared, visible and ultraviolet ranges and steady and alternating electrical fields. Furthermore, a liquid crystal mesophase in the temperature range from at least 0° C. to +50° C., and preferably from −10° C. to +70° C., and a viscosity at room temperature of not more than 60 cP are demanded for liquid crystal materials which can be used industrially. Finally, these materials must not have any characteristic adsorption in the visible range, that is, they must be colorless.

A number of liquid crystal compounds which meet the stability requirements demanded of dielectrics for electronic components and which are also colorless are already known. These include, in particular, the p,p'-disubstituted phenyl benzoates described in German Offenlegungsschrift No. 2,139,628 (U.S. Pat. No. 4,002,670), the p,p'-disubstituted biphenyl derivatives described in German Offenlegungsschrift No. 2,356,085 (U.S. Pat. No. 3,947,375) or the phenylcyclohexane derivatives described in German Offenlegungsschrift No. 2,636,684 (U.S. Pat. No. 4,130,502).

In these categories of compounds and also in other known series of compounds having a liquid crystal mesophase, there are no individual compounds which form a liquid crystal nematic mesophase in the required temperature range from 0° C. to 60° C. Therefore, as a rule, mixtures of two or more compounds are prepared in order to obtain substances which can be practically used as liquid crystal dielectrics. For this purpose, usually at least one compound having a low melting point and clear point is mixed with another compound having a significantly higher melting point and clear point. This usually gives a mixture which has a melting point at a temperature lower than or about the same as the melting point of the component having the lower melting point, while the clear point is between the clear points of the components. Such components having higher melting points and clear points which have been used hitherto are, for example, 4,4''-di-substituted phenyl p-benzoyloxybenzoates of Formula (III)

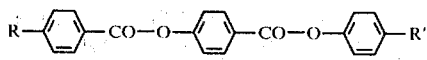

or the biphenyl ester derivatives of Formula IV

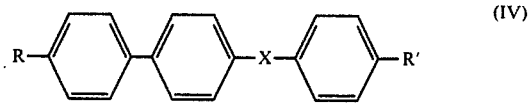

wherein R and R' are alkyl or alkoxy and X is carbonyloxy. The compounds of Formula (III) have not, however, been employed in a wide field of application because they impart a high viscosity to the liquid crystal dielectrics containing them; as a result, the switching times of the liquid crystal display elements produced with these compounds are prolonged in an undesirable manner. It is true that this effect is not so pronounced when the biphenyl esters of Formula (IV) are used, but these compounds, in particular at low temperatures, are not as readily soluble in the most important liquid crystal base materials as is desirable if the clear point is to be raised.

SUMMARY OF THE INVENTION

Accordingly, it is an object of the present invention to provide liquid crystal dielectrics which have a wide temperature range for the nematic phase, which includes room temperature, and which have a viscosity which is as low as possible, and to provide components for such dielectrics which enable such properties.

Upon further study of the specification and appended claims, further objects and advantages of this invention will become apparent to those skilled in the art.

These objects have been achieved by this invention by providing fluorophenylcyclohexanes of Formula (I)

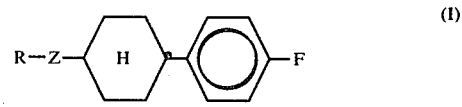

wherein R is alkyl of 1–17 carbon atoms and Z is carbonyl or methylene.

The dielectrics of this invention are formed by admixing one or more of the fluorophenylcyclohexanes of this invention, as components which lower the viscosity, to know liquid crystal substances with a high viscosity.

DETAILED DISCUSSION

The fluorophenylcyclohexanes of Formula (I) generally have monotropic liquid crystalline properties, i.e., their clear point is at a lower temperature than their melting point. Their nematic phase can thus be observed only in a supercooled melt, so that they cannot be used as dielectrics for liquid crystal display elements without other mixing components. However, they are very readily soluble in known liquid crystal mixtures. Furthermore, they lower the viscosity of such substances to such an extent that with the dielectrics resulting therefrom, liquid crystal display elements having short switching times which could scarcely be achieved hitherto can be realized.

The present invention thus relates to the fluorophenylcyclohexanes of Formula (I) and to processes for their preparation. The present invention furthermore relates to the use of the fluorophenylcyclohexanes of Formula (I), mixed with other liquid crystal substances, as dielectrics in liquid crystal display elements.

The present invention also relates to dielectrics, for liquid crystal display elements, with at least two liquid crystal components, of which at least one is a fluorophenylcyclohexane of Formula (I). The invention further relates to electrooptical display elements based on a liquid crystal cell, in which the liquid crystal cell contains a dielectric containing a fluorophenylcyclohexane of Formula (I).

The fluorophenylcyclohexanes of Formula (I) are either ketones of the Formula (Ia)

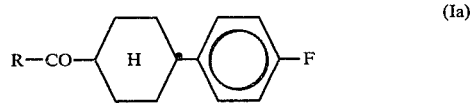

wherein R is as defined for Formula (I), or 4-(4-alkylcyclohexyl)-fluorobenzenes of the Formula (Ib)

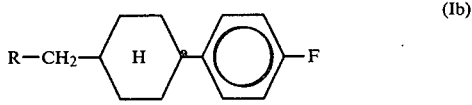

wherein R is also as defined for Formula (I). In all the fluorophenylcyclohexanes of Formulae (I), (Ia) and (Ib) according to this invention, the particular substituents in the 1-positions and 4-positions of the cyclohexane rings are arranged in the trans configuration; in the formulae, this is indicated by the black marking on the right-hand side of the cyclohexane rings.

Generally, the ketones of Formula (Ia) have a lower dielectric anisotropy than the 4-(4-alkylcyclohexyl)-fluorobenzenes of Formula (Ib). The ketones of (Ia) are thus preferably used in dielectrics for liquid crystal display elements which operate on the basis of the phenomena of dynamic scattering or of deformation of oriented phases. The compounds of Formula (Ib) are correspondingly preferably used in dielectrics with a positive dielectric anisotropy, which are employed in display elements based on the twisted nematic cell. However, if technical criteria, such as those of the dielectric anisotropy or also, for example, of the solubility, play a minor role in selecting the compounds according to this invention, compared with economic viewpoints, the ketones (Ia) are preferred, since they can be prepared more simply than the compounds of formula (Ib).

The substituent R in the compounds of Formula (I) can be straight-chain or branched alkyl. If R is straight-chain, that is to say, methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl or n-heptadecyl, the corresponding compounds of Formula (I) as a rule have higher clear points. Furthermore, the starting materials for their syntheses are more readily accessible than are the starting materials for compounds with a branched substituent R. These compounds, including those in which R is straight-chain alkyl with 1 to 12 carbon atoms, preferably 3 to 10 carbon atoms, are thus particularly preferred in the context of this invention.

However, in some cases compounds of Formula (I) with a branched substituent R are also important, since these sometimes have better solubility properties in the customary liquid crystal base mixtures. Such substituents R which are not straight-chain preferably contain not more than one chain branching. Preferred branched substituents R are those in which the carbon chain is branched at the carbon atom adjacent to the group Z or at one of the next two carbon atoms. Among these substituents, those branched groups in which a methyl or ethyl group is in the 1-, 2-, or 3-position on a longer carbon chain are of importance, examples being isopropyl, 1-methylpropyl, 2-methylpropyl, 1-methylbutyl, 2-methylbutyl, 3-methylbutyl, 1-methylpentyl, 1-ethylpentyl, 2-methylpentyl, 1-methylhexyl, 2-ethylhexyl or 1-methylheptyl.

The 4-(4-alkylcyclohexyl)-fluorobenzenes of Formula (Ib) of this invention can be prepared analogously to the 4-alkyl-1-phenyl-cyclohexanes described in German Offenlegungsschrift No. 2,636,684 (U.S. Pat. No. 4,130,502) whose disclosures are incorporated by reference herein.

However, the fluorophenylcyclohexanes of this invention are preferably prepared by a process in which cyclohexene and fluorobenzene are reacted with a carboxylic acid halide of Formula (II)

wherein R is as defined above and Hal is chlorine or bromine, in the presence of a Lewis acid and, if appropriate, in the presence of an inert solvent, at a temperature of $-50°$ to $+100°$ C.; and, in the compound of Formula (Ia) initially obtained, the carbonyl group is optionally reduced to a methylene group in fully conventional manner.

Preferred suitable carboxylic acid halides of Formula (II) are the chlorides, which can be prepared from the corresponding fatty acids in a simple conventional manner, for example by reaction with thionyl chloride.

Lewis acids preferably used in the process of this invention are aluminum chloride, boron trifluoride, zinc chloride, iron trichloride or antimony pentachloride. Aluminum chloride is preferred for economic reasons.

In principle, all the customary solvents for Friedel-Crafts reactions can be used as solvents for the process of this invention. Carbon tetrachloride, methylene chloride, 1,2-dichloroethane, carbon disulfide, petroleum ether, n-hexane or cyclohexane are preferably employed. However, the reaction can also be carried out in the absence of an additional solvent. In this case, it has proved preferable to use an excess of fluorobenzene.

The reaction can be carried out at a temperature of $-50°$ to $+100°$ C. Advantageously, a lower temperature, preferably $-30°$ to $+10°$ C., is chosen at the start of the reaction and the reaction mixture is allowed to warm up to room temperature towards the end of the reaction. In some cases, it is favorable to warm the mixture up to the boiling point of the solvent used, for a short time at the end of the reaction in order to bring the reaction to completion.

The mixture is worked up in a manner which is in itself conventional, preferably by hydrolysis with aqueous hydrochloric acid at temperatures of $-10°$ to $+20°$ C.; extraction of the formed ketone of Formula (Ia), with a suitable organic solvent, for example toluene; and fractional distillation of the extract under reduced pressure. The ketones of Formula (Ia) thus prepared can be used as components of liquid crystal dielectrics without further purification; if purification is desired, the appropriate distillate fractions are preferably recrystallized from methanol or ethanol.

The reduction of the ketones (Ia) to the corresponding 4-(4-alkylcyclohexyl)-fluorobenzenes (Ib) is effected in a manner which is in itself known, for example with hydrazine hydrate and an alkali metal hydroxide or alcoholate in a high-boiling solvent, such as diethylene glycol or dimethylsulfoxide, with zinc and hydrogen chloride in diethyl ether, or with zinc amalgam in aqueous hydrochloric acid. After conventional working up, the compounds of Formula (Ib) thus obtained are purified by fractional distillation under reduced pressure or by recrystallization from a suitable solvent, for example, ethanol or ethyl acetate.

In the preparation method involving the Friedel-Crafts reaction followed by the optional reduction, only the trans-conformation of a cyclohexyl ring is obtained in each case. Hence, no separation of isomers is required.

The dielectrics of this invention consist of two or more components, including at least one of Formula (I). The other components are preferably nematic or nematogenic substances from the categories of azobenzenes, azoxybenzenes, biphenyls, Schiff's bases, in particular benzylidene derivatives, phenyl benzoates, phenylcyclohexanes, optionally halogenated stilbenes, diphenylacetylene derivatives, diphenylnitrones and substituted cinnamic acids. The most important compounds which can be used as other components of this type are of the Formula (V):

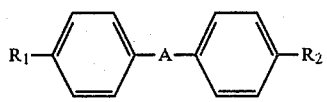

wherein A is

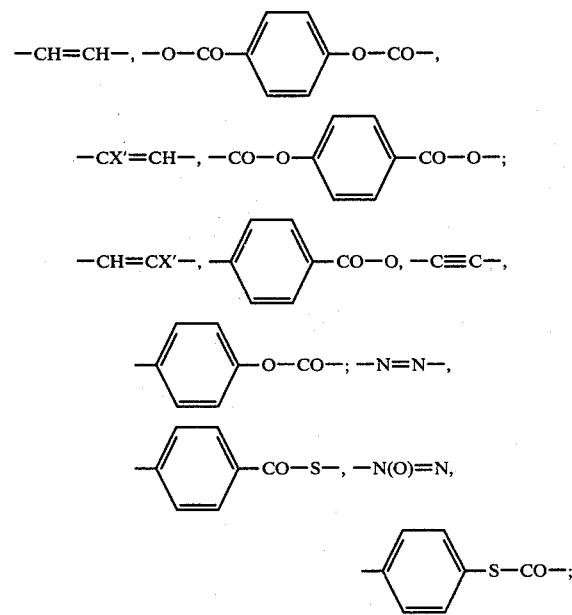

$-N=N(O)-$, $-CH=N-$, $-O-CO-$, $-N=CH-$, $-CO-O-$, $-CH=N(O)-$; $-S-CO-$, $-N(O)=CH-$; $-CO-S-$ or a $C-C$ single bond.

If A is $-CO-O-$, $-O-CO-$ or a C—C single bond, one of the two phenyl rings can also be replaced by a trans-cyclohexyl ring. X' is halogen, preferably Cl. $R_1$ and $R_2$ are identical or different and can be alkyl, alkoxy, alkanoyl, alkanoyloxy or alkoxycarbonyloxy radicals, each of up to 18, preferably up to 8, C atoms; furthermore, one of these radicals can also be a cyano, nitro or isonitrile group. In most of these compounds, $R_1$ and $R_2$ are preferably different, and one of the radicals is usually an alkyl or alkoxy group. However, a large number of other variants of the envisaged substituents are also customary. Many such nematic substances are commercially available.

The liquid crystal dielectrics of this invention generally contain at least 1 and at most 35% by weight of one or more fluorophenylcyclohexanes of Formula (I). Those materials which contain 3 to 30, and preferably 5 to 20% by weight of at least one fluorophenylcyclohexane of Formula (I) are preferred. The viscosity of the liquid crystal base materials is lowered by an average of 10–50% by these additives. The switching times of liquid crystal display elements produced using the dielectrics of this invention are correspondingly shortened. The clear points of the dielectrics of this invention are indeed lower than those of the liquid crystal base materials. However, by suitable choice of the base materials and of the amount of fluorophenylcyclohexane(s) of Formula (I) added, mixtures are obtained which have clear points which are not surpassed even under the warming which occurs during continuous operation of the display elements produced with these mixtures. If the addition of one or more fluorophenylcyclohexanes of Formula (I) to a liquid crystal base material produces a mixture with a clear point which is too low for industrial application, this effect can be compensated, if appropriate, by adding 1–30, and preferably 2–20% by weight of one or more biphenyl esters of Formula (IV), of one or more hexahydroterphenyls according to German Offenlegungsschrift No. 2,701,591 (U.S. Pat. No. 4,154,697) or of one or more of the cyclohexane derivatives according to German Offenlegungsschrift No. 2,800,553 (U.S. Pat. No. 4,229,315.

By means of suitable additives, the liquid crystal dielectrics of this invention can be modified in such a way that they can be used in all the types of display elements disclosed hitherto. Such additives are known to those skilled in the art and are described in detail in the relevant literature. For example, substances for changing the dielectric anisotropy and/or the orientation of the nematic phases can be added. Such substances are described, for example, in German Offenlegungsschriften Nos. 2,209,127 (UK No. 1,376,115), 2,321,632 and 2,611,453 (U.S. Pat. No. 4,077,900), whose disclosures are incorporated by reference herein.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

A mixture of 82 g of cyclohexene and 132 g of n-heptanoyl chloride is added dropwise to a suspension of 160 g of aluminum chloride in 192 g of fluorobenzene over the course of 2 hours, while stirring and cooling to −10°. The reaction mixture is subsequently stirred at +20° for an additional 16 hours and then poured into a mixture of 300 g of ice and 300 ml of fuming hydrochloric acid. The organic phase is separated off, the aqueous phase is extracted twice more, with 200 ml of toluene each time, and the combined organic phases are dried over calcium chloride and distilled. After distilling off the excess fluorobenzene and the toluene, the residue is distilled under reduced pressure (5–10 mm Hg). A first fraction of about 10% of the residue is discarded as first runnings; the subsequent 4-(trans-4-n-heptanoyl-cyclohexyl)-fluorobenzene distilled off, which makes up about 65% of the residue, is taken up in the same amount by volume of methanol and the product is crystallized at −20°; yield 73 g, m. 47°.

The following compounds are obtained analogously:
4-(trans-4-acetylcyclohexyl)-fluorobenzene,
4-(trans-4-propionylcyclohexyl)-fluorobenzene, m. 48°,
4-(trans-4-n-butyrylcyclohexyl)-fluorobenzene,
4-(trans-4-isobutyrylcyclohexyl)-fluorobenzene,
4-(trans-4-n-pentanoylcyclohexyl)-fluorobenzene, m. 35°,
4-(trans-4-(2-methylbutyryl)-cyclohexyl)-fluorobenzene,
4-(trans-4-(3-methylbutyryl)-cyclohexyl)-fluorobenzene,
4-(trans-4-n-hexanoylcyclohexyl)-fluorobenzene,
4-(trans-4-(2-methylpentanoyl)-cyclohexyl)-fluorobenzene,
4-(trans-4-(3-methylpentanoyl)-cyclohexyl)-fluorobenzene,
4-(trans-4-(2-methylhexanoyl)-cyclohexyl)-fluorobenzene,
4-(trans-4-(2-ethylpentanoyl)-cyclohexyl)-fluorobenzene,
4-(trans-4-n-octanoylcyclohexyl)-fluorobenzene,
4-(trans-4-n-nonanoylcyclohexyl)-fluorobenzene, m. 54°,
4-(trans-4-(3-ethylheptanoyl)-cyclohexyl)-fluorobenzene,
4-(trans-4-n-decanoylcyclohexyl)-fluorobenzene,
4-(trans-4-n-undecanoylcyclohexyl)-fluorobenzene,
4-(trans-4-n-dodecanoylcyclohexyl)-fluorobenzene,
4-(trans-4-n-tridecanoylcyclohexyl)-fluorobenzene,
4-(trans-4-n-tetradecanoylcyclohexyl)-fluorobenzene, m. 68°, clp. 10°;
4-(trans-4-n-pentadecanoylcyclohexyl)-fluorobenzene,
4-(trans-4-n-hexadecanoylcyclohexyl)-fluorobenzene,
4-(trans-4-n-heptadecanoylcyclohexyl)-fluorobenzene and
4-(trans-4-n-octadecanoylcyclohexyl)-fluorobenzene.

EXAMPLE 2

A solution of 58 g of 4-(trans-4-n-heptanoylcyclohexyl)-fluorobenzene, 45 g of potassium hydroxide and 30 g of hydrazine hydrate in 200 ml of diethylene glycol is warmed from 100° to 195° over the course of 3 hours. After cooling the reaction mixture, 300 ml of water are added and the mixture is extracted with 200 ml of methylene chloride. The solvent and, as an azeotrope with the solvent, the residual moisture are distilled off from the extract and the 4-(trans-4-n-heptylcyclohexyl)-fluorobenzene which remains is recrystallized from ethyl acetate; yield 47 g, m. 35°, clp. −15°.

The following compounds are obtained analogously:
4-(trans-4-ethylcyclohexyl)-fluorobenzene,
4-(trans-4-n-propylcyclohexyl)-fluorobenzene, m. 32°, clp −40°,
4-(trans-4-n-butylcyclohexyl)-fluorobenzene,
4-(trans-4-isobutylcyclohexyl)-fluorobenzene,
4-(trans-4-n-pentylcyclohexyl)-fluorobenzene, m. 36°, clp. −25°,
4-(trans-4-(2-methylbutyl)-cyclohexyl)-fluorobenzene,
4-(trans-4-(3-methylbutyl)-cyclohexyl)-fluorobenzene,
4-(trans-4-n-hexylcyclohexyl)-fluorobenzene,
4-(trans-4-(2-methylpentyl)-cyclohexyl)-fluorobenzene,
4-(trans-4-(3-methylpentyl)-cyclohexyl)-fluorobenzene,
4-(trans-4-(2-methylhexyl)-cyclohexyl)-fluorobenzene,
4-(trans-4-(2-ethylpentyl)-cyclohexyl)-fluorobenzene,
4-(trans-4-n-octylcyclohexyl)-fluorobenzene,
4-(trans-4-n-nonylcyclohexyl)-fluorobenzene, m. 39°, clp. −5°,
4-(trans-4-(3-ethylheptyl)-cyclohexyl)-fluorobenzene,
4-(trans-4-n-decylcyclohexyl)-fluorobenzene, m. 46°, clp. −5°,
4-(trans-4-n-undecylcyclohexyl)-fluorobenzene,
4-(trans-4-n-dodecylcyclohexyl)-fluorobenzene,
4-(trans-4-n-tridecylcyclohexyl)-fluorobenzene,
4-(trans-4-n-tetradecylcyclohexyl)-fluorobenzene, m. 57°, clp. +15°,
4-(trans-4-n-pentadecylcyclohexyl)-fluorobenzene,
4-(trans-4-n-hexadecylcyclohexyl)-fluorobenzene,
4-(trans-4-n-heptadecylcyclohexyl)-fluorobenzene and
4-(trans-4-n-octadecylcyclohexyl)-fluorobenzene.

The examples which follow relate to liquid crystal dielectrics of this invention:

EXAMPLE 3

A mixture of 27% of 4-(trans-4-n-propylcyclohexyl)-benzonitrile, 39% of 4-(trans-4-n-pentylcyclohexyl)-benzonitrile, 13% of 4-(trans-4-n-pentylcyclohexyl)-4'-cyanobiphenyl and 21% of 4-(trans-4-N-nonylcyclohexyl)-fluorobenzene has a nematic phase in the temperature range from −10° to +55°. The dielectric anisotropy is +10.2 and the viscosity is 20 cSt. The corresponding dielectric which contains no fluorophenylcyclohexane of this invention but is otherwise identical in composition has a viscosity of 32 cSt.

The dielectrics of this invention are outstandingly suitable for use in display elements based on the twisted nematic cell.

EXAMPLE 4

A mixture of 24% of 4-(trans-4-n-butylcyclohexyl)-benzonitrile, 16.5% of 4-ethyl-4'-cyanobiphenyl, 12.0% of 4-n-propoxy-4'-cyanobiphenyl, 17.5% of 4-(trans-4-n-pentylcyclohexyl)-4'-cyanobiphenyl, 7% of 4'-cyanophenyl 4-(trans-4-n-pentylcyclohexyl)-benzoate and 23% of 4-(trans-4-n-heptylcyclohexyl)-fluorobenzene has a nematic phase in the temperature range from −6° to +61°. The dielectric anisotropy is +12.5 and the viscosity is 32 cSt. The corresponding dielectric which contains no fluorophenylcyclohexane of this invention but is otherwise identical in composition has a viscosity of 40 cSt.

The dielectrics of this invention are very suitable for display units based on the twisted nematic cell, and in particular also in the form of matrix displays.

EXAMPLE 5

A mixture of 47% of 4-(trans-4-n-propylcyclohexyl)-1-n-butyryloxybenzene, 19% of 4-n-propylcyclohexyl 4-(trans-4-n-butylcyclohexyl)-benzoate, 14% of 4-n-propylcyclohexyl 4-(trans-4-ethylcyclohexyl)-benzoate and 20% of 4-(trans-4-propionylcyclohexyl)-fluorobenzene has a nematic phase in the temperature range from −5° to +65°. The dielectric anisotropy is −0.2 and the viscosity is 30 cSt. The corresponding dielectric which contains no fluorophenylcyclohexane of this invention but is otherwise identical in composition has a viscosity of 36 cSt.

The dielectrics of this invention are very particularly suitable for display elements which operate on the basis of dynamic scattering.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A fluorophenyl-trans-cyclohexane of the formula

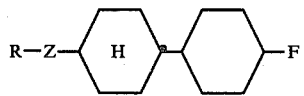

wherein R is alkyl of 1 to 17 carbon atoms and Z is carbonyl or methylene.

2. A fluorophenylcyclohexane of claim 1, wherein R is a straight-chain alkyl group.

3. A fluorophenylcyclohexane of claim 2, wherein R is of 1–12 carbon atoms.

4. A fluorophenylcyclohexane of claim 1, wherein Z is carbonyl.

5. A fluorophenylcyclohexane of claim 1, wherein Z is methylene.

6. A liquid crystal dielectric comprising two components, wherein at least one component is a fluorophenylcyclohexane of claim 1.

7. A liquid crystal dielectric comprising 1–35% by weight of a fluorophenylcyclohexane of claim 1 and a second liquid crystalline component.

8. The liquid crystalline dielectric of claim 6 containing a liquid crystalline component of the formula

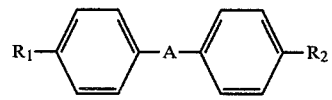

wherein A is

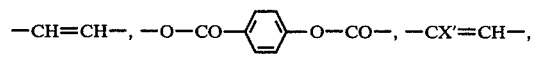

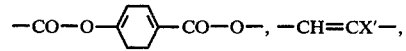

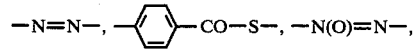

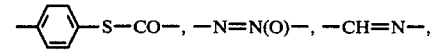

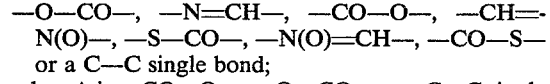

—O—CO—, —N=CH—, —CO—O—, —CH=N(O)—, —S—CO—, —N(O)=CH—, —CO—S— or a C—C single bond;

when A is —CO—O—, —O—CO— or a C—C single bond, one of the two phenyl rings can also be replaced by a trans-cyclohexyl ring; X′ is halogen; $R_1$ and $R_2$ are identical or different and each is alkyl, alkoxy, alkanoyl, alkanoyloxy or alkoxycarbonyloxy, each of up to 18 carbon atoms, and one of $R_1$ or $R_2$ can also be cyano, nitro or isonitrile.

9. An electrooptical display element comprising a liquid crystalline cell having as its liquid crystal dielectric, the liquid crystal dielectric of claim 6.

* * * * *